United States Patent [19]

Shearer et al.

[11] Patent Number: 5,514,556
[45] Date of Patent: May 7, 1996

[54] METHOD FOR DETECTING IMMUNE DYSFUNCTION IN ASYMPTOMATIC AIDS PATIENTS AND FOR PREDICTING ORGAN TRANSPLANT REJECTION

[75] Inventors: Gene M. Shearer, Bethesda; Mario Clerici, Rockville; Charles S. Via, Ellicott City, all of Md.

[73] Assignee: The United States of America as represented by The Department of Health and Human Services, Washington, D.C.

[21] Appl. No.: 185,423

[22] Filed: Jan. 19, 1994

Related U.S. Application Data

[60] Division of Ser. No. 535,407, Jun. 8, 1990, Pat. No. 5,344,755, which is a continuation-in-part of Ser. No. 341,360, Apr. 21, 1990, abandoned.

[51] Int. Cl.[6] ............................ C12Q 1/02; G01N 33/53
[52] U.S. Cl. ............................................. 435/7.24; 435/29
[58] Field of Search ...................................... 435/7.24, 29

[56] References Cited

U.S. PATENT DOCUMENTS 5,344,755   9/1994   Shearer et al. .......................... 435/5

OTHER PUBLICATIONS

W. J. Herbert et al, Dictionary of Immunology–3rd Ed., Blackwell Scientific Publications, 1985, p. 114.
C. S. Via et al, *Journ. Immunol.*, 144, 2524–2528, 1990.

*Primary Examiner*—David Saunders
*Attorney, Agent, or Firm*—Townsend and Townsende and Crew

[57] ABSTRACT

A sensitive and accurate tissue culture system and kit fop detecting subtle changes in immune function is provided. The system is based on the comparison of IL-2 production by T helper cells in response to recall antigens including influenza A virus, tatanus toxoid, alloantigens, mouse xenogeneic antigens and the like or combinations thereof. Different stages of immune dysfunction can be differentiated and organ graft rejection can be predicted by the method of the present invention.

1 Claim, 10 Drawing Sheets

KEY:
- MED
- FLU
- ALLO
- TET
- XENO
- PHA

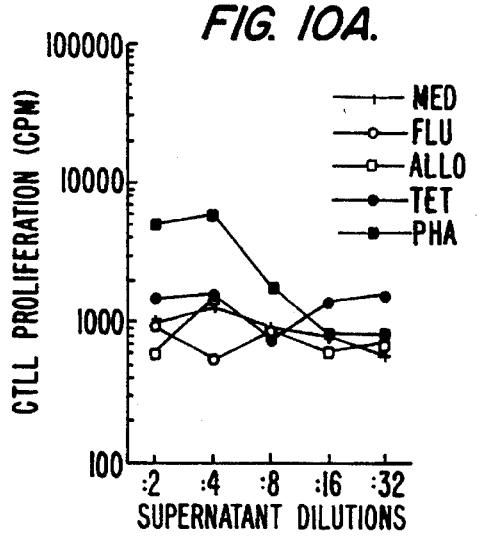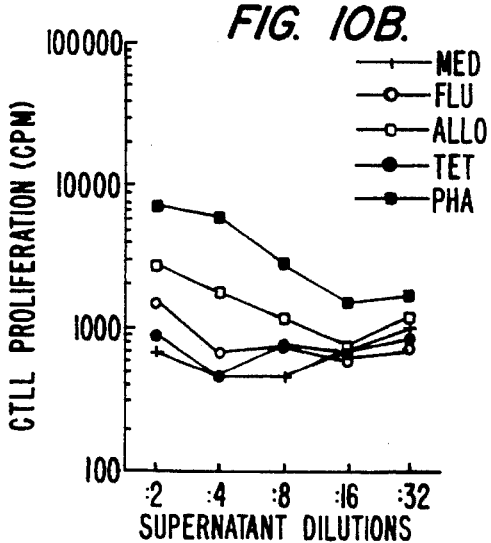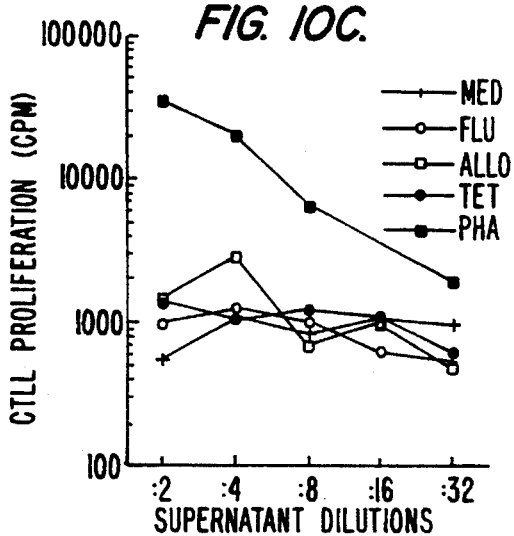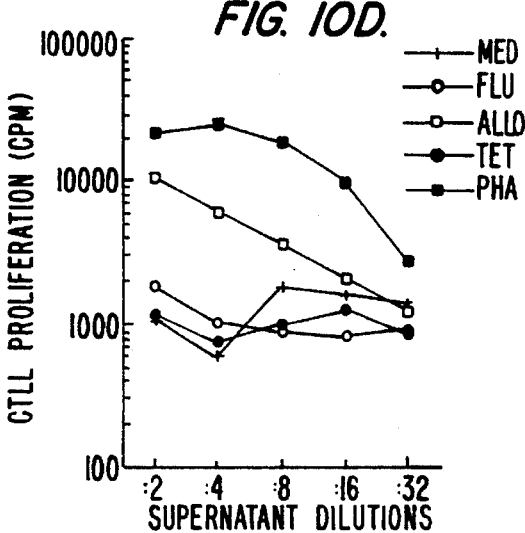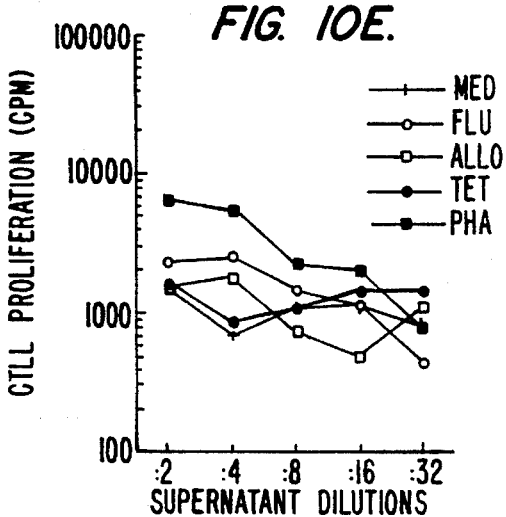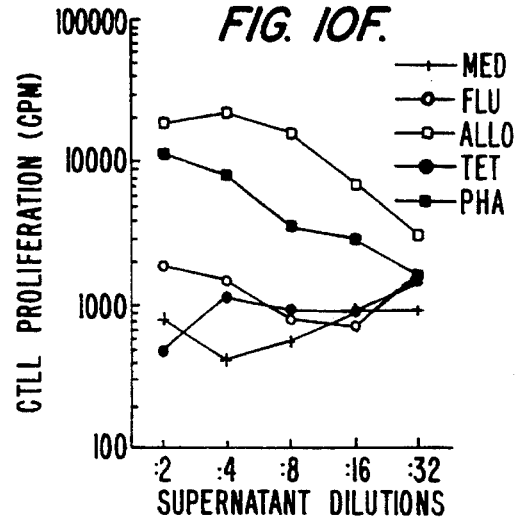

METHOD FOR DETECTING IMMUNE DYSFUNCTION IN ASYMPTOMATIC AIDS PATIENTS AND FOR PREDICTING ORGAN TRANSPLANT REJECTION

This is a division of application Ser. No. 07/535,407 filed Jun. 8, 1990 and now U.S. Pat. No. 5,344,755, which is a continuation in part of application Ser. No. 07/341,360 filed Apr. 21, 1990 and now abandoned.

The present invention is related to providing a sensitive and accurate tissue culture system that detects subtle changes in immune function prior to appearance of symptoms or conditions resulting from immune dysfunction or dysregulation.

It is known that AIDS patients die as a consequence of the failure of the immune system. Certain types of cancers, drug-induced immune deficiencies and disorders related to autoimmunity are some examples of conditions that result from immune dysfunction. It is vitally important in such cases to detect and characterize the earliest possible changes in immune function so that timely intervention can take place to control, identify and treat the anomalous condition.

So far, the detection of an immune deficient state in HIV-infected individuals who are not yet diagnosed with AIDS has relied mainly on in vitro generated T lymphocyte responses to agents such as mitogens and lymphocytes from other donors. These stimuli activate not only the T lymphocyte population that is primarily affected by HIV (T4 cells), but also other T lymphocytes (T8 cells), which are not affected by HIV early in progression toward AIDS. Studies have been reported using recall antigens, which detect immune deficiency before the development of AIDS (Lane et al. *N. Engl. J. Med.* 313:79, 1985; Shearer et al. *J. Immunol.* 137:2514, 1986). However, there is no method in these reports to determine or estimate the time interval between the first detection of an immune defect and progression to AIDS. Therefore, one does not know how early before AIDS diagnosis such defects were detected, nor whether these defects represented stages in the progression toward AIDS. Moreover, although these earlier studies measured certain T lymphocyte-mediated functions, they did not employ a direct measure of T helper cell function (which is considered to be the primary defect in AIDS patients). Furthermore, the use of recall antigens can give misleading results, because failure to respond to recall antigens (which by definition require previous and sometimes recent exposure of the patient to the antigen) could be due not to HIV-induced immune deficiency, but rather to the patient not having been previously or recently exposed to the recall antigen used in the test. Moreover, prior art assays for immune abnormalities in asymptomatic HIV-infected individuals do not recognize the possibility of multiple distinct categories of dysfunction.

In short, the limitations or disadvantages of the prior art tests are as follows: 1) The time interval for first detection of immune deficiency and development of AIDS symptoms has not been established: 2) A direct measure of T helper cell function by assaying for lymphokine production was not performed; 3) Recall antigens were used in most studies, which are dependent on prior and possibly recent antigenic exposure; and 4) Multiple and distinct stages in the loss of T helper cell function that are predictive for progression toward the disease were neither detected nor characterized.

SUMMARY OF THE INVENTION

It is, therefore, an object of the present invention to provide a kit for an in vitro direct test of T helper cell function based on antigen-induced IL-2 production.

It is a further object of the present invention to provide a method for detecting early signs of dysfunction in individuals afflicted with one of several different immune system abnormalities.

It is another object of the present invention to provide a method for detecting early signs of immune dysfunction in individuals asymptomatic of AIDS.

It is an additional object of the present invention to provide immune functional analysis to distinguish at least three distinct stages of T lymphocyte dysfunction in AIDS.

Other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 10A–10F shows the T helper cells tests of asymptomatic, HIV⁺ patients before and one month after initiation of AZT therapy. The data from three different patients are shown before therapy (left panels) and one month after AZT therapy (right panels). In all three patients the IL-2 response to ALLO was elevated after only one month of AZT treatment.

DETAILED DESCRIPTION OF THE INVENTION

Figure 1A:
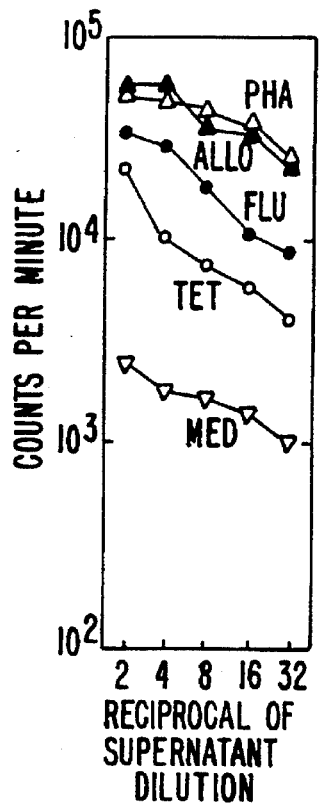
FIGS. 1A–1J shows IL-2 production by PBL from two HIV-control donors (A, F), four Walter Reed stage 1 HIV$^+$ individuals (B–E), and four Walter Reed stage 2 HIV$^+$ individuals (G–J). The PBL from these donors were unstimulated (MED. ▽) or were stimulated with FLU (o), TET (o), ALLO (▲), or PHA (Δ). The titration curves represent the dilutions of culture supernatant used to stimulate the CTLL.
Figure 1B:
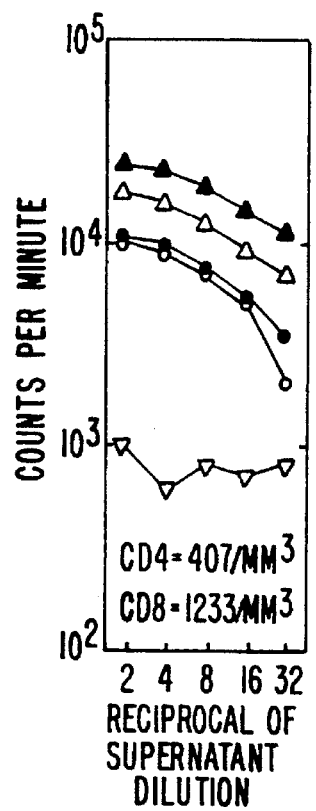
Figure 1C:
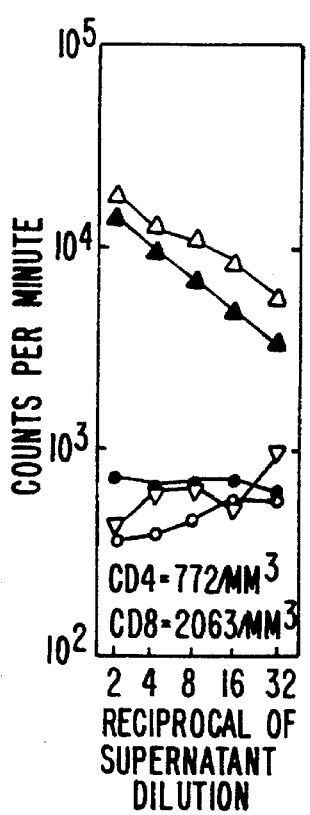
Figure 1D:
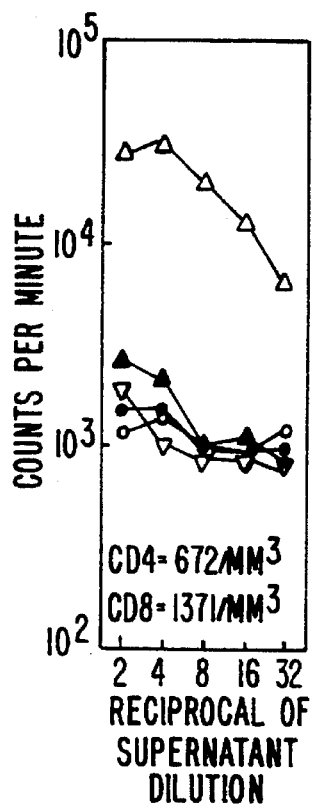
Figure 1E:
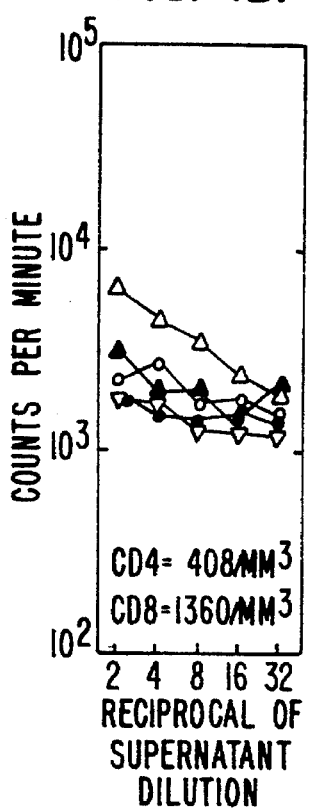
Figure 1F:
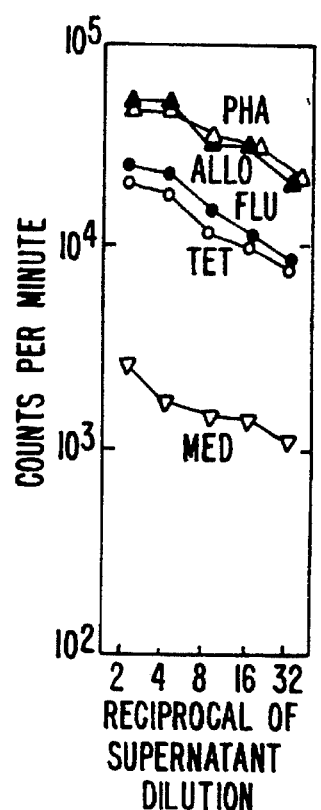
Figure 1G:
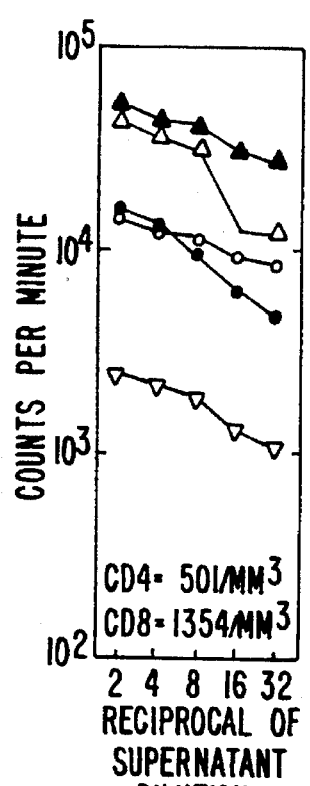
Figure 1H:
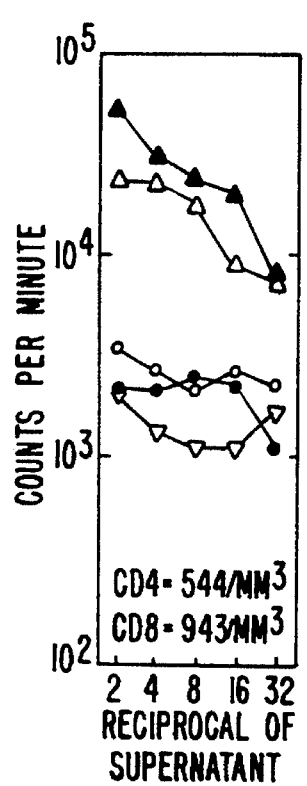
Figure 1I:
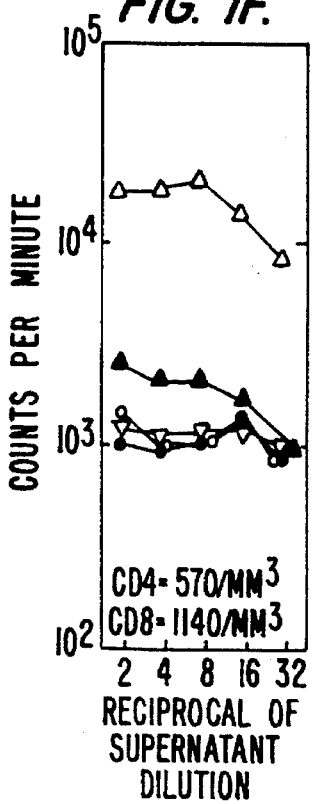
Figure 1J:
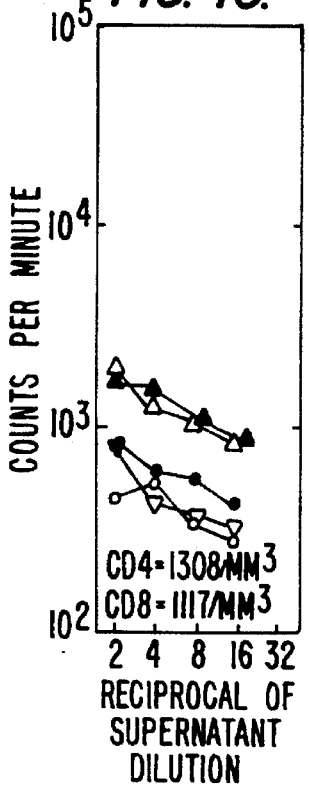
Figure 2A:
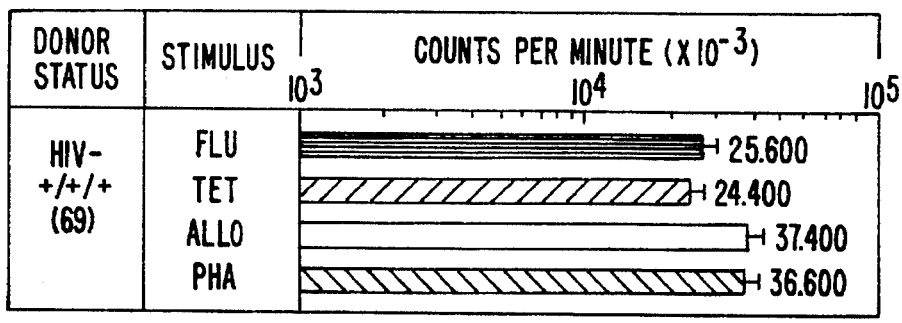
FIGS. 2A–2E shows the mean and standard error values of IL-2 production (detected at a supernatant dilution of 1:4) by PBL from HIV$^-$ (top panel) and HIV$^+$ (three lower panels) individuals to FLU (■), TET (▨), ALLO (□), and PHA (▧). +/+/+ indicates individuals whose PBL generated normal IL-2 responses to all four stimuli: –/+/+ indicates individuals whose PBL were selectively deficient in IL-2 responses to FLU and TET: –/–/+ indicates individuals whose PBL were deficient in IL-2 responses to FLU, TET, and ALLO, but not to PHA; –/–/– indicates individuals whose PBL were deficient in response to all four stimuli. Number of donors tested is shown in ( ) in donor status column.
Figure 2B:
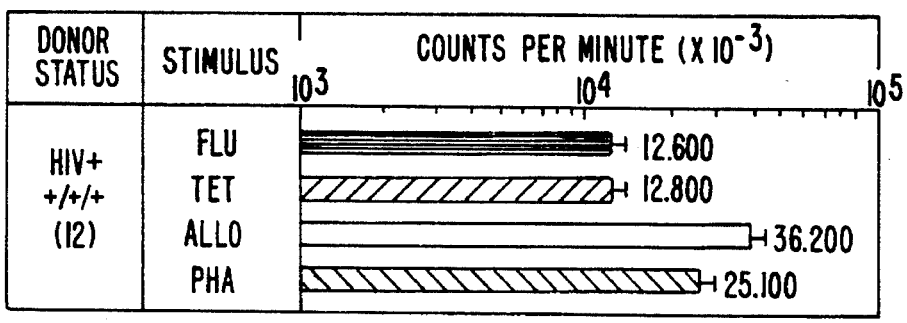
Figure 2C:
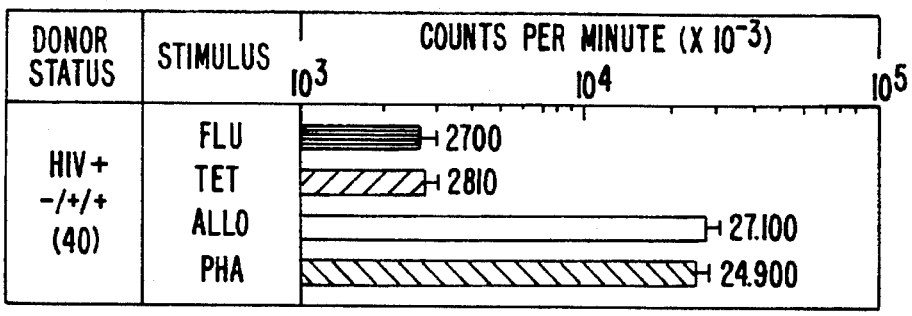
Figure 2D:
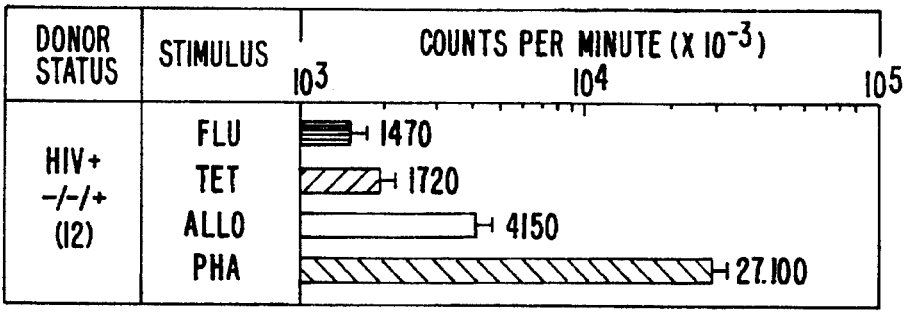
Figure 2E:
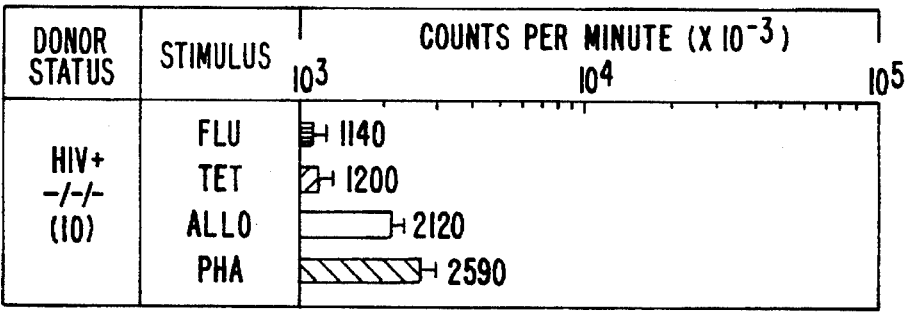

The above and various other objects and advantages of the present invention are achieved by a sensitive in vitro test for T helper cell function by measuring IL-2 production to the recall antigens, such as influenza A virus, tetanus toxoid, alloantigens and mouse xenogeneic antigens in human peripheral blood leukocytes (PBL) from control and affected individuals.

Unless defined otherwise, all technical and scientific terms used herein have the same meaning as commonly understood by one of ordinary skill in the art to which this invention belongs. Although any methods and materials similar or equivalent to those described-herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

In the present study, the T helper cell ($T_H$) function of peripheral blood leukocytes (PBL) from Walter Reed Stage 1 (WR 1) and 2 (WR 2) patients was tested directly by evaluating in vitro production of interleukin-2 (IL-2) following stimulation with influenza virus (FLU), tetanus toxoid (TET), mouse xenoantigens (XENO), alloantigens (ALLO), and phytohemagglutinin (PHA). This panel of stimuli was selected for study because $T_H$ responses to FLU, TET and XENO have been recently shown to be MHC self-restricted and require CD4⁺ $T_H$ and autologous antigen presenting cells (APC). In contrast, the $T_H$ response to ALLO and PHA can utilize both CD4⁺ and CD8⁺ T helper cells. Using this approach, three categories of $T_H$ dysfunction were identified among HIV⁺ patients whose clinical stages were WR 1 or WR 2.

GENERAL PROCEDURES AND MATERIALS

Antigen:

Influenza A virus was prepared by infecting chicken eggs with a stock of influenza A virus, and the allantoic fluid was harvested, aliquoted and frozen at −70° C. Tetanus toxoid was obtained from a commercial source (Massachusetts Department of Health, Boston, Mass.). Mouse lymphocytes were prepared from the spleens of any strain of mouse for use as xenoantigens. Human peripheral blood leukocytes (PBL) from any healthy donor that is HLA-mismatched with the patient were used as a source of alloantigens. Optimal stimulatory doses of each antigen were determined using PBL from healthy, uninfected donors. Mouse and human cell lines grown continuously in vitro could also be prepared and used as a commercial resource. Phytohemagglutinin A (PHA) (GIBCO, Grand Island, N.Y.) was used for mitogen stimulation.

Preparation of Lymphocytes for Testing:

PBL from HIV-infected patients and uninfected controls donors were prepared from whole blood drawn by venopuncture. The PBL were separated by Lymphocyte Separating Medium (Organon Teknika Corp., Durham, N.C.) and centrifugation at 1800 rpm for 20 minutes, followed by two washings in RPMI- 1640 media (GIBCO, Grand Island, N.Y.). The PBL were either tested immediately, and/or were cryopreserved (at a freezing rate of 1° C./minute) in liquid nitrogen.

Generation of T Helper Cell Responses:

PBL were diluted in RPMI-1640 medium containing 5% AB⁺ human plasma, and cultured with the above-mentioned stimuli at a concentration of $3 \times 10^6$ cells/well in 2 ml. 24-well Linbro plates (Flow Laboratories Inc., McClean, Va.). The PBL were cultured with the various antigens for one week (in the presence of anti-TAC monoclonal antibody, provided by Dr. Thomas Waldmann, NIH, to prevent consumption of IL-2 by the stimulated PBL). Supernatants were collected at the end of 7 days of culture and were frozen for later testing for IL-2 content. The supernatants were subsequently thawed and diluted through five 2-fold dilutions with RPMI-1640 media, and were added to 96-well plates (Flow Laboratories, McClean, Va.) for microcultures of the IL-2 dependent CTLL cell line (American Type Tissue Culture Collection, Rockville, Md.), which requires IL-2 for cell proliferation and growth. ³H-thymidine (ICN Inc., Irvine, Calif.) was added to the CTLL cultures 24 hr after addition of the supernatants, and incorporation of the isotope was quantatively determined to measure the IL-2 content of the initial culture supernatants. The concentrations of antigens used for stimulation were: influenza A virus, 1:1000; tetanus, 1:1000; PHA, 1:200; HLA allogeneic and mouse xenogeneic stimulating cells were irradiated with 5000 rad, and added at $2 \times 10^6$/ml.

It is pointed out that although $3 \times 10^6$ PBL has been used herein per test, the tests could be performed with $2 \times 10^5$ PBL or less which is more desirable for clinical use.

Patients and Clinical Evaluation

Individuals were diagnosed as being HIV infected if they had anti-HIV antibodies demonstrated by the HIV enzyme immuno-assay (Abbott Laboratories, Irving, Tex.) and confirmed by Western blot analysis (Roche Biomedical Laboratories, Burlington, N.C.). Western blots were considered positive if they showed at least two of the following three bands reactive: p24, gp41, and gp120 or gp160. Patients were classified according to the Walter Reed Staging System (Redfield et al. The Walter Reed staging classification for HTLV-III/LAV infection. N Engl J Med 1986: 314:131–2). Walter Reed stage 0 denotes seronegative, high-risk individuals such as sexual contacts of persons with documented HIV infection. WR 1 denotes an individual who is seropositive for HIV, but has more than 400 $CD4^+$ T-helper cells/$mm^3$: WR 2 is similar to WR 1 except that the individuals also have presence of chronic adenopathy of greater than 1 $cm^3$ at $\geq 2$ extra-inguinal sites; WR 3 identifies patients with fewer than 400 $CD4^+$ T helper cells; WR 4 indicates patients who additionally present with impaired delayed skin reactions to a panel of at least two of five recall antigens; WR 5 denotes the presence of complete anergy or oral candidiasis; and WR 6 is a classification of opportunistic infection, diagnostic of CDC defined AIDS.

Lymphocyte counts and T cell subsets were determined using laser-based flow cytometry (Coulter Epics Profile, Coulter Electronics. Inc., Hialeah, Fla.) and OKT4A (anti-CD4) and OKT8 (anti-CD8) monoclonal antibodies (Orthodiagnostics Systems, Raritan, N.J.).

Skin testing for recall antigens was performed using intradermal injections of 0.02 ml of PPD (STU) (Connaught Laboratories, Ontario, Canada), *Candida albicans* (1/500) (Hollister-Stier, Spokane, Wash.), Trichophyton (1/500) (Hollister-Stier, Spokane, Wash.), tetanus toxoid (1/5) (Connaught Laboratories, Ontario, Canada), and mumps (full strength) (Connaught Laboratories, Ontario, Canada).

EXAMPLE 1

In Vitro Tests for $T_H$ Function

Whole blood from $HIV^-$ and $HIV^+$ individuals was drawn in Vacutainer tubes containing preservative-free heparin (Becton-Dickinson, Rutherford, N.J.) and shipped from Lackland, Tex. to Bethesda, Md. overnight at ambient temperature (22°–24° C.) in crushproof containers. PBL were separated on lymphocyte separation medium (LSM: Organon Teknika Corp., Durham, N.C.). The separated PBL were washed twice in phosphate-buffered saline, and the number of viable cells was determined by trypan blue exclusion and hemacytometer. Cells were then resuspended at $3\times10^6$/ml in RPMI 1640 (GIBCO, Grand Island, N.Y.) containing 0.5 percent penicillin and 1 percent glutamine. One ml of PBL was added per well to 24-well flat-bottom Linbro tissue culture plates (Flow Laboratories, Inc., McClean, Va.). The PBL were cultured without stimulation or were stimulated with: a) influenza A/Bangkok RX73 (at a final dilution of 1:1000) as described by Shearer et al. *J Immunol* 1986, 137:2514–21; b) tetanus toxoid (at a final dilution of 40 lf/ml) (Massachusetts Department of Health, Boston, Mass.); c) irradiated (5000 rad) mouse spleen cells ($2\times10^6$/well): d) a pool of irradiated (5000 rad) PBL from two or more unrelated $HIV^-$ donors ($2\times10^6$/well for IL-2 production and $2\times10^5$/well for proliferation); and e) PHA (GIBCO) diluted 1:200. Pooled $AB^+$ plasma was added to each well (final dilution 1:20). Supernatants of stimulated and unstimulated cultures were harvested 7 days later and frozen at −20° C. For studies of IL-2 production, the anti-IL-2 receptor antibody, monoclonal anti-TAC (obtained from Dr. T. A. Waldmann, Metabolism Branch, NCI, NIH, Bethesda, Md.) was added at the initiation of culture at a final concentration of 10 µg/ml, in order to block IL-2 consumption (Uchiyama et al, *J Immunol* 1981, 126:1393–7). The supernatant IL-2 activity was assessed as the ability to stimulate the proliferation of the IL-2-dependent cell line, CTLL. This cell line is stimulated by human IL-2, but not by human IL-4. Assay cultures consisted of $8\times10^3$ CTLL/well and five successive 2-fold dilutions of supernatant. Twenty-four hours later, the cultures were pulsed with 1 Ci of [$^3$H]thymidine (ICN Radiochemicals, Irvine, Calif.) and harvested 18 hours later. Results are expressed as mean cpm for three replicate wells for a given supernatant dilution. Standard errors were always less than 10 percent of the mean values. The concentration of anti-Tac antibody used in the initial culture did not inhibit CTLL proliferation.

Determination of Responsive and Unresponsive Patients

Patients were defined as responsive to a given antigen if the mean cpm of their stimulated cultures was greater than three standard deviations above the mean unstimulated cpm of the $HIV^-$ control donors. The cutoff value for IL-2 production was 7300 cpm and was derived from a mean of 70 $HIV^-$ donors. Supernatant dilutions of both 1:2 and 1:4 were used for determination of responsiveness for the Il-2 assay.

Statistical Analysis of Data

Row (R) x column (C) contingency tables were set up as shown below in Tables 2–4 for testing possible correlations of the four different $T_H$ functional categories with $CD4^+$ cell numbers or WR staging (Snedecor et al, Statistical Methods, 7th Edition. Ames, IA: The University of Iowa Press, 1980). The sum of the $\chi^2$ value was calculated by the sums of the equation $\chi^2=(f-F)^2/F$, where f is the observed frequency and F is the expected frequency. The degrees of freedom for this analysis are: df=(R−1)(C−1). Student t tests were performed for the comparisons of two independent samples of unequal size as described by Snedecor and Cochran (Snedecor et al. supra), and p values were determined.

RESULTS

Patterns of $T_H$ Responses in WR 1 and WR 2 Patients

Peripheral blood leukocytes from 70 $HIV^-$ control donors and 74 $HIV^+$ WR 1 and 2 patients were tested for in vitro production of IL-2 following stimulation with FLU, TET, ALLO, or PHA. The complete IL-2 titration curves for each of these stimuli are presented in FIG. 1 for two $HIV^-$ controls (FIG. 1, panels A and F), four WR 1 patients (FIG. 1, panels B–E), and four WR 2 patients (FIG. 1, panels G–J). The data on these patients were selected from the group of 74 to illustrate four different patterns of IL-2 responsiveness. The first pattern, observed in both WR 1 and WR 2 patients (FIG. 1, panels B and G), is characterized by positive IL-2 responses to all four stimuli. However, in many of the patients, the responses to FLU and TET were moderately below those obtained using PBL from the $HIV^-$ controls (compare FIG. 1, panels B and G with A and F, respectively). In the second pattern. PBL from WR1 and WR2 patients (FIG. 1, panels C and H) generated near normal IL-2 responses to ALLO and PHA, but failed to produce IL-2 in response to FLU and TET. In the third pattern, PBL from the WR1 and WR2 patients shown in FIG. 1, panels D and I, responded to PHA but failed to respond to FLU, TET, and ALLO. Finally, PBL from the WR1 and WR2 patients shown in FIG. 1, panels E and J, failed to respond to any of these stimuli. These results indicate that four different states of $T_H$ function can be identified within WR 1 and WR 2 patients, and that Walter Reed criteria do not predict the in vitro $T_H$ functional potential of these patients. Furthermore, the failure of WR 1 and WR 2 patients to respond to any combination of these stimuli did not appear to be correlated with $CD4^+$ cell numbers (see below).

Using the criteria described herein supra, the number of individuals in the group of 74 patients and 70 controls were determined who responded to FLU, TET, ALLO, or PHA by IL-2 production. Forty-nine of these same patients and 58 of the controls were also tested for proliferative responses to the same stimuli. The numbers and percentages of patients and controls who were unresponsive to each of the stimuli by either of the two $T_H$ tests are presented in Table 1. Sixty-two of the 74 $HIV^+$ donors (84 percent) failed to respond to FLU or TET by the IL-2 test. There was an exact correlation between the IL-2 responses to FLU and TET in that the same 62 patients who failed to respond to FLU also did not respond to TET. A much lower proportion of these donors was unresponsive to ALLO (30 percent), and an even lower proportion was unresponsive to PHA (14 percent). In contrast, only one $HIV^-$ control donor was unresponsive to FLU and TET, and none of the controls was unresponsive to ALLO or PHA. The percent of $HIV^-$ controls that was unresponsive to FLU and TET was only 1 percent. All of the controls responded to ALLO and PHA by both assays. For convenience, those patients who responded to all four stimuli were referred to as +/+/+ (FLU and TET/ALLO/PHA); those who failed to respond to FLU and TET, but responded to ALLO and PHA as −/+/+; those who failed to respond to FLU, TET, and ALLO, but responded to PHA as −/−/+; and those who did not respond to any of the stimuli as −/−/−. It should be noted that no patients were found who: a) responded to FLU or TET but not to ALLO or PHA: or b) did not respond to PHA but were responsive to any of the other three stimuli. These results are compatible with a pattern of sequential progression from +/+/+ to −/+/+, to −/−/+, and finally to −/−/−.

FIG. 2 lists the frequencies of these four categories of $T_H$ responsiveness, and within each category, quantitatively summarizes the IL-2 results obtained from each stimulant. The data shown are for a supernatant dilution of 1:4; similar results were obtained at dilutions of 1:2 and 1:8. Despite the fact that 12 $HIV^+$ patients tested positive for IL-2 production in response to each of the four stimuli (+/+/+), their mean cpm values for FLU and TET stimulation were 2-fold below those of the $HIV^-$ controls (compare FIG. 2, panels A and B). Among the 40 patients who were selectively unresponsive to FLU and TET (−/+/+), IL-2 production levels to FLU and TET were significantly below those of the $HIV^-$ controls (compare FIG. 2, panels C and A; $p<0.01$ for FLU and TET), and also significantly below those of the responsive $HIV^+$ patients (compare FIG. 2, panels C and B: $p<0.05$ for FLU and $p<0.05$ for TET). Responses did not differ significantly among these three groups for responses to ALLO and PHA (FIG. 2, panels A–C), The 12 patients who responded only to PHA by IL-2 production (−/−/+ exhibited a significant reduction in mean cpm for ALLO when compared with the ALLO response of −/+/+ patients or the $HIV^-$ donors (compare FIG. 2, panel D with C and A; $p<0.05$). The mean cpm for response to PHA, however, was equivalent in these two groups. Also, there was a further decline in the magnitude of responses to FLU and TET in −/−/+ patients. Finally, the 10 patients who were unresponsive to any of these four stimuli (−/−/−) exhibited a significant reduction in cpm for IL-2 production to PHA compared to the groups of patients who responded to PHA (compare FIG. 2, panel E with A, B, C, and D; $p<0.05$). There was a further reduction in cpm for response to ALLO in this totally unresponsive group (compare FIG. 2, panel E with D). The results of FIG. 2 verify that these 74 WR 1 and WR 2 patients can be divided into four functional categories, based on $T_H$ responses to recall antigens, alloantigens, and a T-cell mitogen.

Lack of Correlation Between $T_H$ Function and Either $CD4^+$ Cell Number or WR 1 and WR 2

To determine whether there was a correlation between any of the four $T_H$ functional patterns and $CD4^+$ cell numbers of either of the early Walter Reed stages, contingency tables were prepared in which the numbers of patients in each functional category are shown for three ranges of $CD4^+$ cell numbers (Table 1) and for WR 1 and WR 2 patients (Table 2). Patients with $CD^{4+}$ cell numbers below $400/mm^3$ are not included, because such patients are, by definition, in WR 3 or higher. Statistical analysis of the data in the R×C contingency comparison of Table 2 indicate that there was no correlation between any of the four $T_H$ response patterns (by IL-2 or proliferation) and the $CD4^+$ cell numbers. A similar analysis of the frequency data for the four $T_H$ categories by either the IL-2 production or proliferation assays, for $T_H$ function indicates no correlation of function with WR1 or WR2 (Table 2).

Time-Dependent Changes in $T_H$ Function

The data illustrated in FIGS. 1 and 2 suggest a progression from the functional stage in which the patient is responsive to all four stimuli (+/+/+), through a selective loss in $T_H$ function to recall antigens such as FLU and TET (−/+ +), followed by loss of response to ALLO (−/−/+), and finally to a totally unresponsive state (−/−/−). However, these data, as well as the data collected on most of the 74 patients, represent only one point in time for each individual's progression toward symptomatic AIDS.

Figure 3A:
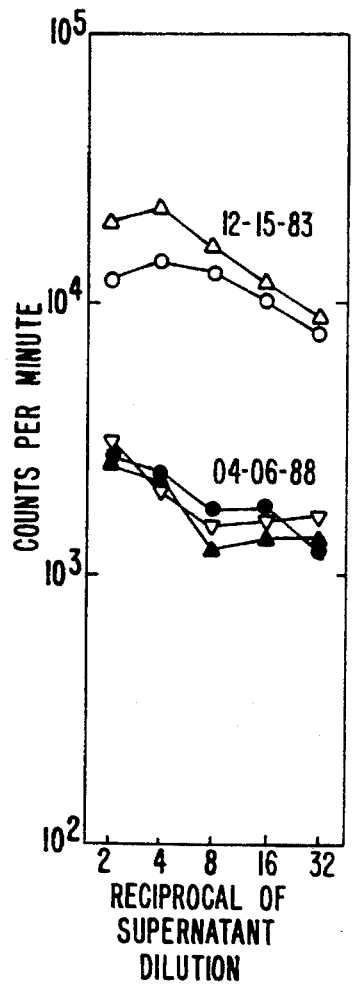
FIGS. 3A–3C shows IL-2 production by PBL from three HIV$^+$ individuals taken at different time intervals during progressive loss of $T_H$ cell function. PBL were unstimulated (▽) (mean value of the two unstimulated cultures), or stimulated with FLU (Δ,▲) or TET (o,●). Open symbols indicate the response from the earlier bleed: closed symbols indicate from the later bleed. The numbers in each panel indicate the two dates that blood was drawn from a donor to be used in the comparative test. Both samples of the PBL from each donor were cryopreserved and tested in the same experiment.
Figure 3B:
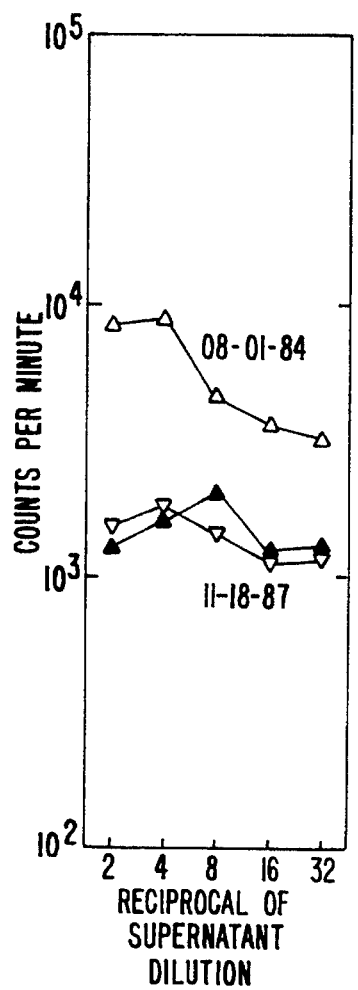
Figure 3C:
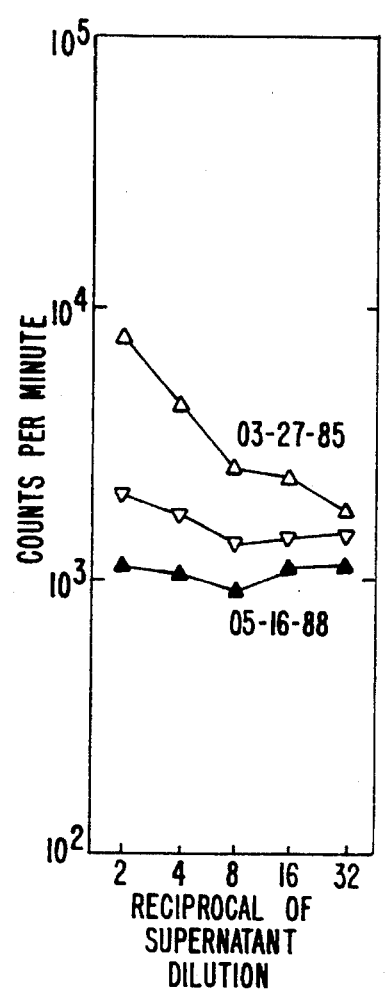

A longitudinal comparison of FLU-stimulated IL-2 production by PBL from three donors who have been involved in this study for several years is shown in FIG. 3. PBL from the donor shown in panel A were cryopreserved in 1983 and in 1988. This donor remained asymptomatic throughout the 4.5-year period and had $573/mm^3$ of $CD4^-$ cells at the time of the last blood collection. PBL from the donor in panel B were cryopreserved in 1984 and in 1987. This donor experienced a reduction in $CD^{4+}$ cells (from 500 to $139/mm^3$) during this period, but was not diagnosed with lymphadenopathy or AIDS. PBL from the donor in panel C were cryopreserved in 1985 and 1988. During this time interval, this donor experienced a reduction in $CD4^-$ cells from 715 to $235/mm^3$, but remained otherwise asymptomatic. The two preparations of PBL from each of these three donors were thawed simultaneously and tested for their ability to generate IL-2 in response to stimulation with FLU and TET (donor in panel A) or with FLU only (donors in panels B and C). The results (FIG. 3) illustrate that all three donors had lost the ability to generate a $T_H$ response to FLU during the 3- to 4.5-year period in which these blood samples were drawn. These results demonstrate that in these three donors there was a time-dependent, selective loss of $T_H$ function to CD4-dependent antigens such as FLU and TET and suggest that a similar pattern of selective loss of $T_H$ response occurred in the other donors who were selectively defective in their responses to FLU and TET. It should be noted that the time-dependent loss of $T_H$ response to FLU and TET in the donor in panel A was not due to a critically low number of CD4$^+$ cells. Due to limitations on the number of cryopreserved PBL available, it was not possible to test these individuals for $T_H$ function to ALLO or PHA.

Figure 4A:
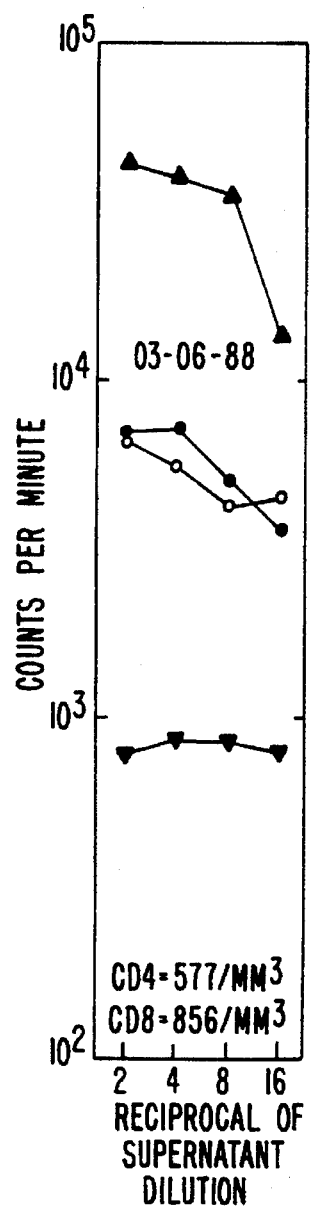
FIGS. 4A–4C shows IL-2 production by PBL from a single asymptomatic. HIV$^+$ individual (WR 1) taken at three four-month time intervals. PBL were unstimulated (▽) or stimulated with FLU (●), TET ( ), ALLO (▲), or PHA (Δ). The numbers in each panel indicate the dates that the blood was drawn and tested. CD4$^+$ and CD8$^+$ cell numbers are shown in the lower part of each panel.
Figure 4B:
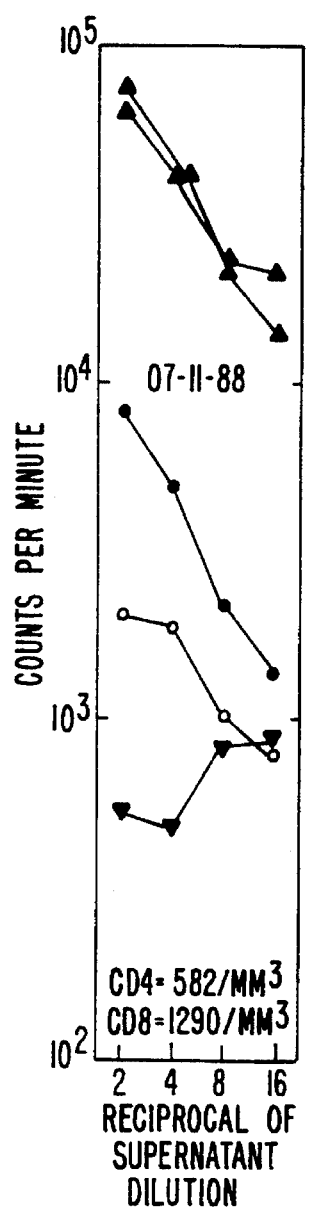
Figure 4C:
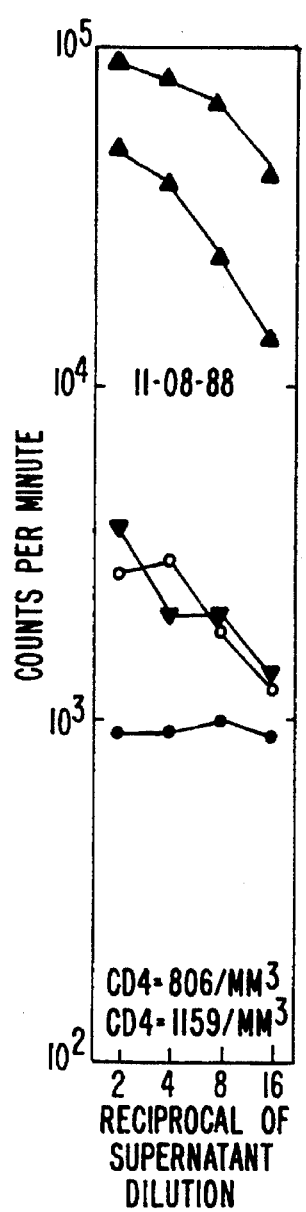
Figure 5A:
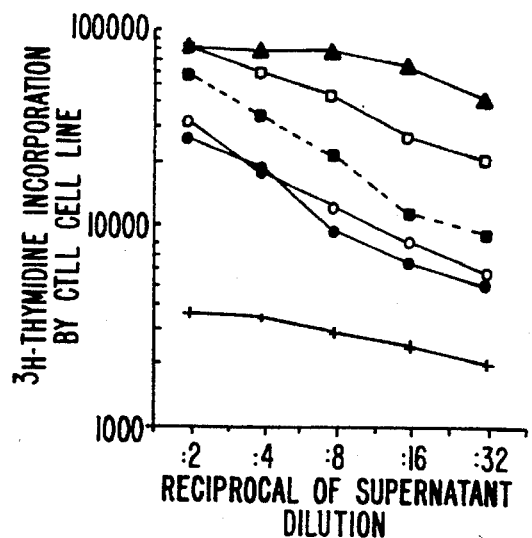
FIGS. 5A–5E compares IL-2 production by PBL from one HIV$^-$ control (A) and four HIV$^+$, WR1 patients (B, C, D, E) for response to FLU (o), TET (●), ALLO (□), PHA (▲), and mouse xenoantigens (XENO) (▨). The titration curves represent the dilutions of culture supernatant used to stimulate the CTLL.
Figure 5B:
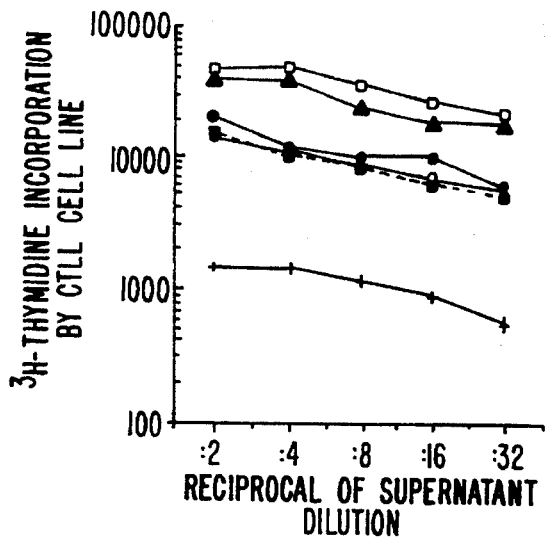
Figure 5C:
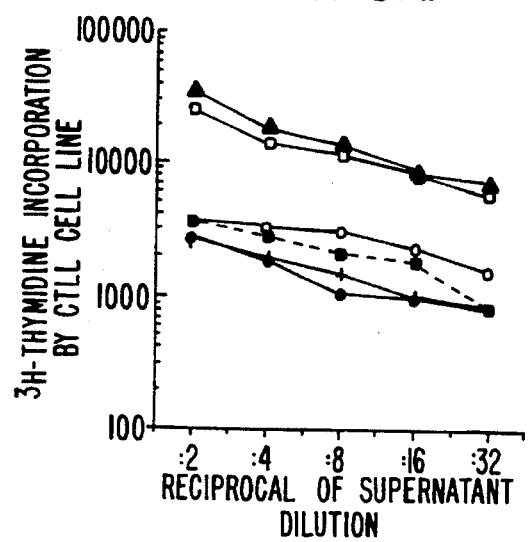
Figure 5D:
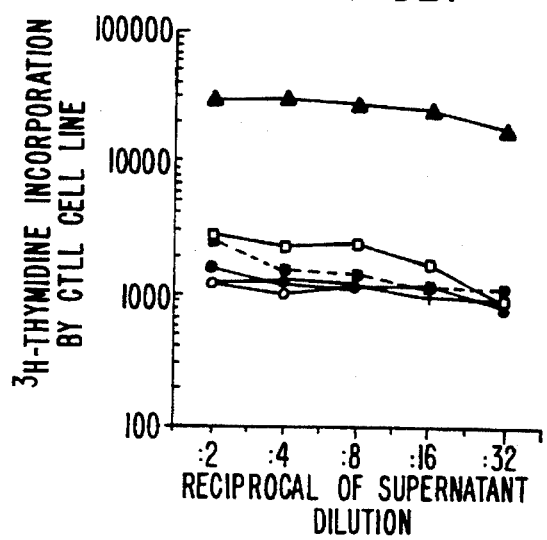
Figure 5E:
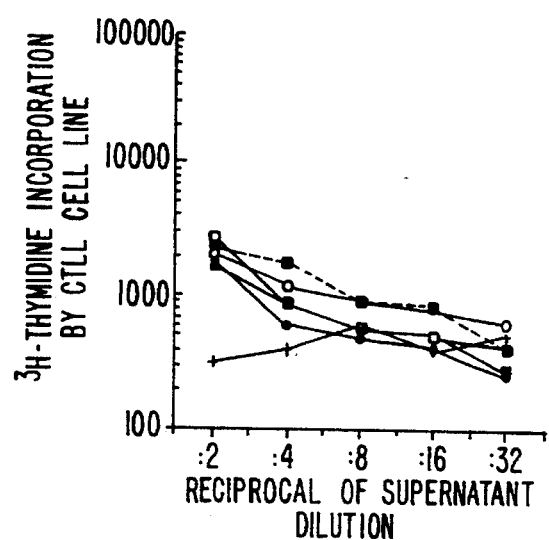

To obtain a more precise time estimate for development of $T_H$ unresponsiveness, an asymptomatic, HIV$^+$ donor was studied at four-month intervals to detect possible loss of $T_H$ function. FIG. 4 illustrates the titration curves for IL-2 production by PBL stimulated with FLU, TET, ALLO, or PHA. In March 1988, the patient was marginally responsive to FLU and TET, but was strongly responsive to ALLO (FIG. 4, panel A). (PHA was not tested in this experiment.) During the next 8 months, the patient's FLU and TET responses continued to decline to unstimulated levels whereas the ALLO and PHA responses remained strong (panels B and C). During this time interval, the patient did not develop any symptoms and CD4$^+$ and CD8$^+$ T cell numbers increased slightly. In all three experiments. PBL from HIV$^-$ control donors generated potent $T_H$ responses to all four stimuli (data not shown). These data demonstrate that loss of $T_H$ function to recall antigens can occur abruptly and are not necessarily associated with symptomatic changes nor with a reduction in CD4$^+$ cell numbers.

To further investigate possible progression in $T_H$ defects, IL-2 responses of PBL from patients in the more advanced WR 3 to WR 6 were studied. If the failure to produce IL-2 in response to ALLO and PHA represents $T_H$ dysfunction associated with more advanced stages of AIDS progression, then it would be expected that a larger proportion of WR 3 to WR 6 patients would be unresponsive not only to FLU or TET, but also to ALLO or PHA. The proportions of IL-2 responses by 22 patients are summarized in Table 3 and are compared with the proportions of responses by our 74 WR 1 and WR 2 patients using the same two stimuli. Whereas 16 percent of the WR 1 and WR 2 patients responded to FLU, 0 percent of the WR 3 to WR 6 patients responded to FLU. Furthermore, fewer WR 3 to WR 6 patients responded to ALLO than did WR 1 and WR 2 patients. In fact, the majority of the WR 3 to WR 6 failed to respond to FLU or ALLO (64 percent) compared with only 30 percent of the WR 1 and WR 2 patients who failed to respond to both stimuli. The statistical likelihood that these frequency differences between WR 1 and WR 2 and WR 3 to WR 6 patients were due to chance was less than 1 percent. Thus, these results demonstrate that the $T_H$ functional phases shown in FIGS. 1 and 2 represent a sequential progression of immune dysfunction that is associated with progression toward AIDS.

It should be pointed out that earlier studies have reported that the $T_H$ and CTL responses to recall antigens may be defective in certain HIV$^+$ patients. For example, Lane et al (N Engl J Med 1985, 313:79–84), using enriched CD4$^+$ T cells from one AIDS patient, demonstrated a qualitative defect in the proliferative response to TET but not to PHA. Smolen et al (J. Clin Invest 1985; 75:1818–34) and Garbrecht et al (Clin Exp Immunol 1987; 67:245–51), respectively, demonstrated defects in IL-2 production and proliferation in patients for the autologous mixed lymphocyte reaction but not to HLA alloantigens. Shearer et al (J Immunol 1986; 137:2514–21) have previously demonstrated a selective defect in CTL responses to FLU but not to ALLO in asymptomatic, HIV$^+$ individuals. Because the deficient CTL response to FLU could be corrected in vitro by recombinant IL-2, the CTL defect appeared to reflect an underlying deficiency in CD4$^+$ $T_H$ function. The present study measures $T_H$ function directly by assessing IL-2 production and extends these findings by: (a) identifying a series of three distinct $T_H$ functional defects in asymptomatic patients: (b) demonstrating a time-dependent progressive and selective loss of $T_H$ function in individual asymptomatic patients; and (c) attempting to correlate these defects with clinical staging criteria.

The three different patterns of $T_H$ dysfunction identified among these asymptomatic patients were (a) a selective loss of $T_H$ function to recall antigens such as FLU and TET, but retention of $T_H$ function upon stimulation to ALLO or PHA (54 percent); (b) an absence of $T_H$ function to the recall antigens and to ALLO, but preserved responses to PHA (16 percent); and (c) a lack of response to all of the stimuli (14 percent). Not all asymptomatic, HIV$^+$ individuals exhibited these defects, because 16 percent of these asymptomatic patients were responsive to all of the stimuli, None of the three patterns of $T_H$ dysfunction could be attributed to a critical reduction in CD4$^+$ cell numbers. In fact, a large proportion of these patients had CD4$^+$ cell frequencies in excess of 600/mm$^3$ (58 percent). It is estimated that the time interval between the onset of the $T_H$ functional defect to recall antigens and identification of AIDS symptoms can be as long as two years, However, the data presented in FIG. 4 (from an asymptomatic WR 1 patient) demonstrate that the selective loss in T4 T helper cell function to recall antigens such as FLU and TET can occur within the relatively short period of eight months and is not associated with a reduction in T4 cell numbers, a parameter commonly used in following HIV-infected patients.

Figure 6:
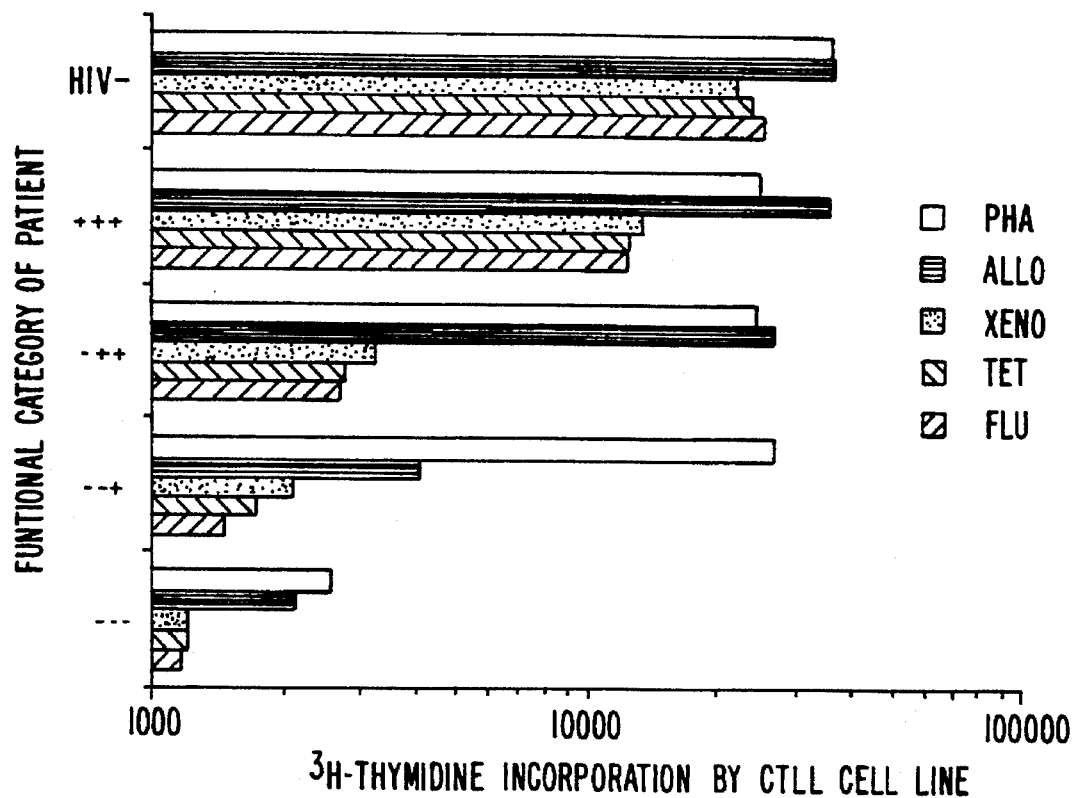
FIG. 6 summarizes the mean values of IL-2 production (detected at a supernatant dilution of 1:4) by PBL from HIV⁻ (upper group of bar graphs) and HIV⁺ (lower four groups of bar graphs) individuals to PHA (□), ALLO (■), XENO (▨), TET (▨), and FLU (▨). +/+/+ indicates individuals whose PBL generated normal IL-2 responses to all five stimuli; –/+/+ indicates individuals whose PBL were selectively deficient in IL-2 responses to FLU, TET, and XENO: –/–/+ indicates individuals whose PBL were deficient in IL-2 responses to FLU, TET, XENO, and ALLO, but not to PHA: –/–/– indicates individuals whose PBL were deficient in response to all five stimuli.

The T helper cell responses to FLU and TET require pre-immunization (i.e. they are recall antigens), whereas the response to allo does not. Thus, failure to respond to FLU and/or TET could reflect lack of recent exposure to these recall antigens rather than necessarily being due to an induced immune defect. To avoid this potential flaw in the detection system, T helper cell reponse to mouse xenoantigens (XENO) has been added to the battery of antigens that are to be used, because it has been found that the response to XENO (which is not a recall antigen) utilizes the same T4 T helper cell pathway used by the recall antigens FLU and TET, but does not use the alternate helper pathways that can be employed by the ALLO response. Therefore, it would be expected that the T helper cell responses of PBL from HIV$^+$ individuals would follow the patterns of FLU and TET and not those of ALLO and PHA. FIGS. 5 and 6 present the evidence. As can be seen, there is an exact concordance between the T helper cell responses of PBL from these patients to FLU, TET and XENO. Thus, the T helper cell response to XENO (a non-recall antigen) can be substituted for the T helper reponses to FLU and TET (both of which require previous immunization).

EXAMPLE 2

Determining the Effect of an Agent on Immune System

Figure 7:
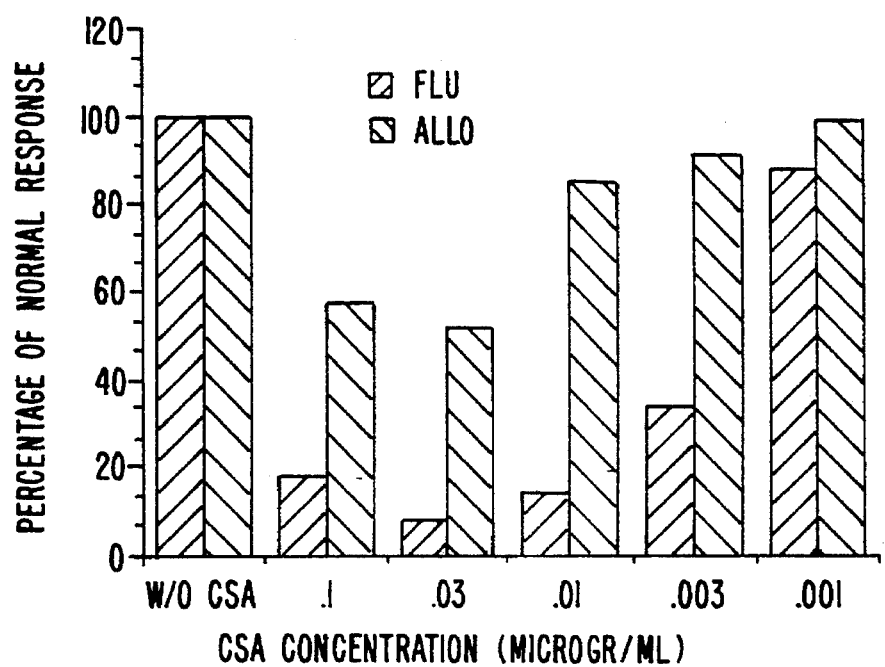
FIG. 7 shows that the FLU response (▨) of PBL from healthy individuals are more sensitive to the in vitro suppressive effects cyclosporin A (CsA) than is the response to ALLO (▨).

Apart from its utility in determining subtle changes on immune system, the present invention is also useful for assessing the effect of an agent on the immune system (for example, an immunosuppressive drug). To demonstrate this utility, the effect of cyclosporin A (CsA), one of the most extensively used immunosuppressive drugs for organ transplantation and treatment of autoimmune diseases, was studied. FIG. 7 shows the results obtained when CsA was added to the in vitro culture. At the lowest concentrations of CsA (0.001 µg/ml), there was no detectable effect on T helper cell function. At the intermediate concentrations of CsA (0.003–0.01 µg/ml), there appeared to be a selective inhibition of T4 helper activity, as demonstrated by the selective loss of responses to FLU and TET, but not to ALLO. The highest concentrations of CsA used (0.03–0.1 µg/ml), abolished T helper activity to FLU and TET and reduced the response to ALLO. These results indicate that different doses of CsA can selectively affect distinct T helper cell pathways, and that the sensitive test system of the present invention can detect these differences. It has also been found that treatment of kidney allograft patients or patients with autoimmune uveitis with certain doses of CsA selectively abrogates T4 T helper cell function (data not shown).

Although the response to ALLO utilizes both the T4 and T8 helper cell pathways, the system of the present invention can be modified so that one can use the ALLO response to detect T4 and T8 helper activity together, or to detect T4 helpers alone, or T8 helpers alone. This modification comprises depletion of the responding PBL of APC by adherence to plastic tissue culture flasks (Costar. Inc., Cambridge, Mass.) and nylon fiber (Fenwal Laboratories, Deerfield, Ill.), prior to stimulation with ALLO. Such treatment results in abrogation of the T4-self restricted T helper pathway, and the ALLO response that results is mediated by T8 helper cells. Alternatively, depletion of the allogeneic stimulator cells by adherence to plastic and nylon fiber results in abrogation of the T8 helper response, and the resulting ALLO response is mediated by self-restricted T4 helper cells. The use of this approach is important because it permits analysis of distinct allo-specific T helper cell pathways, which are relevant for detecting pathway-selective effects of immuno-suppressive drugs, as well as for detecting the T helper cell pathways that are responsible for foreign tissue graft rejection.

In summary, a sensitive in vitro test has been developed for T helper cell function using lymphokine production (IL-2) to the recall antigens influenza A virus, tetanus toxoid, and to alloantigens, and mouse xenogeneic antigens. Using this system, one can detect a spectrum of subtle immune defects that occur in asymptomatic, HIV-infected patients, in patients with autoimmune diseases, in lymphoid cancers, as well as in kidney allograft patients who are on immuno-suppressive drugs. Furthermore, the sensitivity of this system lends it as a prognostic indicator for progression toward AIDS, and as a predictor of graft rejection. Based on the data presented herein, the value of the present invention to the medical community for providing a sensitive and accurate evaluation of immune function (that is of minimal risk and discomfort to the patient) for several clinical conditions that involve immune dysregulation is quite apparent.

Some specific applications of the principles and methodology described herein are now illustrated.

Figure 8:
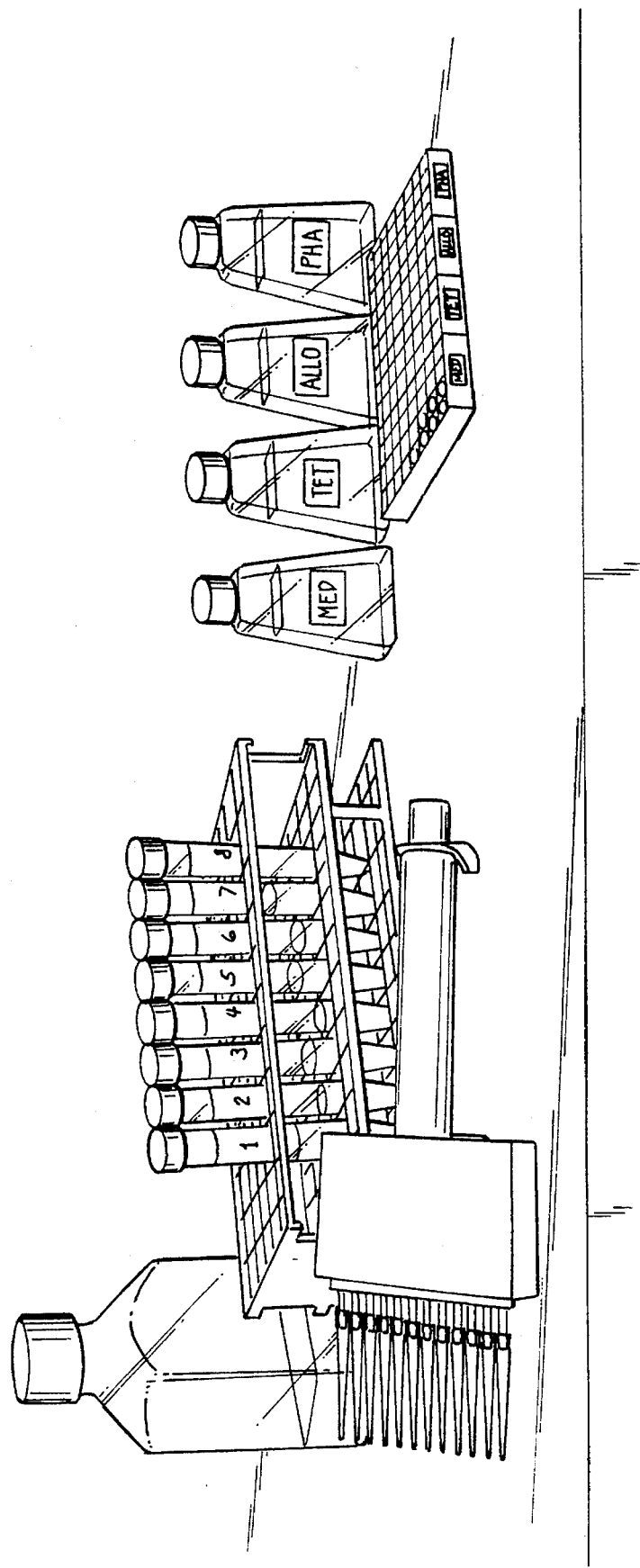
FIG. 8 shows photograph of a 96-well microtiter plate kit that would test leukocytes from eight patients for T helper cell-antigen presenting cell function for unstimulated (medium, MED) and for three T cell stimuli (tetanus toxoid, TET; HLA allogeneic cells, ALLO; and the T cell mitogen, phytohemagglutinin, PHA).
Figure 9:
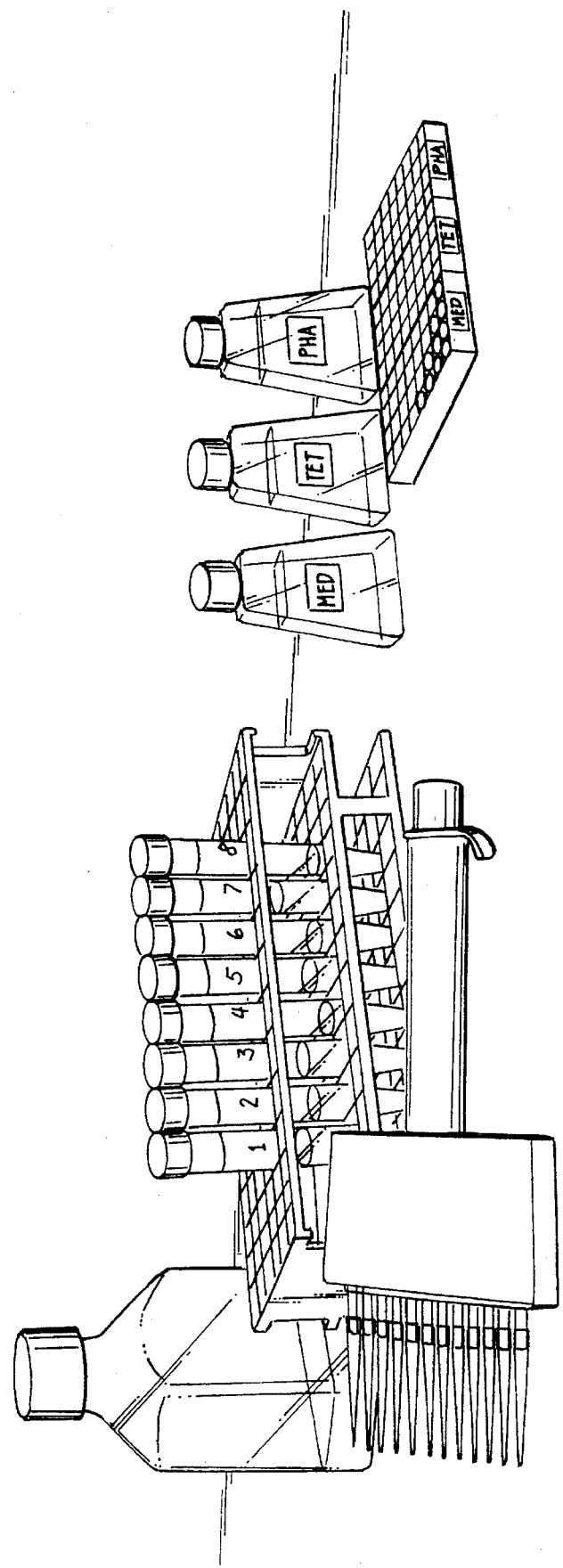
FIG. 9 shows photograph of a modified 96-well microtiter plate kit that would test leukocytes from eight patients for T helper cell-antigen presenting cell function for MED, TET and PHA. Unlike the kit in FIG. 8, lyophylyzed preparations of TET and PHA could be incorporated on the plate prior to distribution.

Preparation of a Kit for Testing In Vitro T Helper-Antigen Presenting Cell Function In accordance with the present invention, a kit has been prepared that could be used for testing T helper cell function. Photographs of this kit and a modification of it are shown in FIGS. 8 and 9. A 96-well, sterile, flat bottom, clear, plastic plate (with lid) of the type produced by Costar, Cambridge, Mass., catalog number 3596 is used. The plate can be divided into eight rows, with four groups of triplicate wells in each row. To each of the eight rows would be added leukocytes from a single blood donor (patient or control donor) (at $1\times10^5$ to $3\times10^5$ leukocytes per well in a 0.1 ml volume). These rows of leukocytes would be testified for proliferative or IL-2 responses when unstimulated (medium, MED), or when stimulated with tetanus toxoid (TET), irradiated foreign or "allogeneic" leukocytes (ALLO), or with the T cell mitogen phytohemagglutinin (PHA). The medium and various stimuli are added in 0.1 ml volume, diluted in culture medium containing 5% pooled human plasma from healthy donors. Thus, each row of 12 wells permits triplicate cultures of leukocytes from one patient for one group of unstimulated cells, and for groups of cells activated with the three different stimuli (TET vs ALLO vs PHA). Each of the eight rows of 12 wells permits the testing of eight different patients per plate. The cultures are stimulated in a moist, 87° C., 3% $CO_2$ Incubator.

The cultures tested for IL-2 production should contain the anti-TAC IL-2 receptor monoclonal antibody to block IL-2 production: the cultures to be assayed for proliferation should not contain the anti-TAC reagent (Clerici, et al. 1989 J. Clin. Invest. 84:1892). Supernatants from the IL-2 cultures are collected, diluted and assayed on the IL-2-dependent CTLL line, for content of IL-21. Cells in the proliferative cultures are pulsed with $^3$H-thymidine for 18 hours, harvested and the $^3$H-thymidine is determined.

As illustrated in FIG. 8, each 96-well plate permits the testing of T-helper cells' function for eight different patients for negative control and for three different T-cell stimuli. Such analysis permits functional T-helper cell characterization that detects four distinct categories of immune function. The total number of PBL required per patients for this analysis is in the range of $1.2\times10^6$ to $3.6\times10^6$. To demonstrate clinical application, the system of the present invention was used to successfully characterize T-helper cell function in 30 pediatric AIDS patients for whom the number of leukocytes is very limiting (data not shown). Thus, the system has been scaled to a level that permits the testing of patients who can provide only small volumes of blood.

Of course, as mentioned above, the kit employs standardized preparation of various stimuli. Thus, frozen preparation of concentrated or diluted preparations of such stimuli as TET, ALLO and PHA are provided. Therefore, a modification of the kit would be to prepare 96-well plates in which optimal concentrations of lypholyzed TET and PHA are already contained in the plates, and only PBL and medium would need to be added. However, it would not be possible to add lypholysed HLA allogeneic cells to these plates because the particular T helper cell defect, which can be detected using ALLO, requires intact and viable allogeneic antigen presenting cells.

Another modification would be a kit in which alloantigenic stimulation is omitted from the test kit, which permits the use of lypholyzed TET and PHA (see FIG. 2). Clearly, this modification would exclude the detection of one of the categories of immune dysfunction.

A protocol for the treatment of asymptomatic, HIV$^+$ patients with AZT was initiated by the NIAID, NIH in 1988, and was terminated in August 1989, because it appeared that AZT therapy was effective in retarding the progression of the asymptomatic patients toward symptomatic AIDS. Our laboratory was able to obtain blood samples before and one month after initiation of AZT treatment of a small number of asymptomatic patients enrolled in this protocol. The limited and preliminary results shown in FIG. 3 indicate that after only one month of AZT therapy, in vitro tests for T helper cell function indicated a significant restoration of immune function. Such results clearly indicate that the kit described herein can be used to detect improved immune function resulting from drug therapy, even as early as one month after initiation of therapy.

Early Detection of Kidney Allograft Rejection

In order to determine the reliable predictability of the system of the present invention, blood leukocytes from six patients who were transplanted with foreign kidney grafts were tested. The findings, summarized in Table 4, indicate that only two of the six patients were responsive to HLA alloantigens (ALLO) by the $CD4^-$ Th-self pathway. In contrast, five of the six patients were responsive via their $CD4^-$ Th-alloAPC pathway, and all six were responsive via the $CS8^-$ Th-alloAPC pathway. Most remarkable was the fact that two of the patients were undergoing chronic kidney graft rejection, and these two patients were the only ones (#2 and #3) whose leukocytes responded to HLA alloantigens via the $CD4^-$ Th-selfAPC pathway. There was no correlation between rejection, and the presence or absence of either of the other two pathways. It should be noted that the in vitro Th-APC tests were performed by a scientist who did not know that two patients were undergoing chronic graft rejection. These results indicate that this in vitro Th-APC pathway test is predictive for foreign tissue graft rejection in patients. The fact that the test was a predictor of rejection even in chronic rejectors and did not require an acute rejection phase, also indicates that this test is very sensitive and may serve as an early warning for graft rejection.

A method for predicting organ transplant rejection in accordance with the present invention, comprises the steps of: (a) obtaining a sample of peripheral blood leukocytes from an organ transplant recipient candidate; (b) then determining in said sample the presence of immune deficiency in the 4- self pathway by stimulating said leukocytes with alloantigen after depleting responder leukocytes of antigen-presenting cells, the presence of immune deficiency in said 4- self pathway being predictive of non-rejection of organ transplant and the absence of immune deficiency in said 4- self pathway being predictive of acute or chronic organ transplant rejection.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

Lack of Correlation Between $T_H$ Function and $CD4^+$ Cell Number

| Functional category* | RANGE OF $CD4^+$ CELL NUMBERS (/mm³): | | | | STATISTICS |
|---|---|---|---|---|---|
| | 400–600 | 600–800 | >800 | TOTAL | |
| By IL-2 production: | | | | | |
| +/+/+ | 6 | 2 | 4 | 12 | $x^2 = 4.60$ |
| −/+/+ | 14 | 16 | 10 | 40 | $p > 0.50$ |
| −/−/+ | 4 | 5 | 3 | 12 | |
| −/−/− | 7 | 2 | 1 | 10 | |
| Total: | 31 | 25 | 18 | 74 | |

TABLE 1-continued

Lack of Correlation Between $T_H$ Function and $CD4^+$ Cell Number

| Functional category* | RANGE OF $CD4^+$ CELL NUMBERS (/mm³): | | | | STATISTICS |
|---|---|---|---|---|---|
| | 400–600 | 600–800 | >800 | TOTAL | |
| By proliferation: | | | | | |
| +/+/+ | 3 | 2 | 5 | 10 | $x^2 = 7.73$ |
| −/+/+ | 11 | 13 | 4 | 28 | $p > 0.25$ |
| −/−/+ | 3 | 4 | 2 | 9 | |
| −/−/− | 2 | 0 | 0 | 2 | |
| Total: | 19 | 19 | 11 | 49 | |

*+/+/+ indicates patients who responded to FLU, TET, ALLO, and PHA;
−/+/+ indicates patients who responded to ALLO and PHA, but not to FLU and TET;
−/−/+ indicates patients who responded to PHA, but not to FLU, TET, or ALLO;
−/−/− indicates patients who did not respond to any of the four stimuli.

TABLE 2

Lack of Correlation between $T_H$ Function and Walter Reed Stage (WR)

| Functional category* | WR | | TOTAL | STATISTICS |
|---|---|---|---|---|
| | 1 | 2 | | |
| By IL-2 production: | | | | |
| +/+/+ | 6 | 6 | 12 | $^2 = 1.71$ |
| −/+/+ | 22 | 18 | 40 | $p > 0.50$ |
| −/−/+ | 6 | 6 | 12 | |
| −/−/− | 8 | 2 | 10 | |
| Total: | 42 | 32 | 74 | |
| By proliferation: | | | | |
| +/+/+ | 3 | 7 | 10 | $^2 = 3.84$ |
| −/+/+ | 15 | 13 | 28 | $p > 0.25$ |
| −/−/+ | 5 | 4 | 9 | |
| −/−/− | 2 | 0 | 2 | |
| Total: | 25 | 24 | 49 | |

*+/+/+ indicates patients who responded to FLU, TET, ALLO, and PHA;
−/+/+ indicates patients who responded to ALLO and PHA, but not to FLU and TET;
−/−/+ indicates patients who responded to PHA, but not to FLU, TET, or ALLO;
−/−/− indicates patients who did not respond to any of the four stimuli.

TABLE 3

Evidence for a Progressive and Sequential Loss of $T_H$ Function in More Advanced Walter Reed Stages (WR)*

| $T_H$ response to: | | Fraction and percentage of patients in: | |
|---|---|---|---|
| FLU | ALLO | WR 1 and 2 | WR 3–6 |
| + | + | 12/74 (16%) | 0/22 (0%) |
| − | + | 40/74 (54%) | 8/22 (36%) |
| − | − | 22/74 (30%) | 14/22 (64%) |

*$x^2 = 9.82$; $p < 0.07$

TABLE 4

Correlation between a positive response by the
CD4+ Th-self APC pathway and chronic kidney graft rejection.

| Patient Number | Th-APC pathway response | | | Rejection of Kidney? |
|---|---|---|---|---|
| | CD4+Th-selfAPC | CD4+Th-alloAPC | CD8+Th-alloAPC | |
| 1 | negative | positive | positive | No |
| 2 | positive | positive | positive | Yes |
| 3 | negative | positive | positive | No |
| 4 | negative | positive | positive | No |
| 5 | positive | positive | positive | Yes |
| 6 | negative | negative | positive | No |

What is claimed is:

1. A method for predicting organ transplant rejection, said method comprising:

obtaining a sample of peripheral blood leukocytes from an organ transplant recipient;

exposing said peripheral blood leukocytes to allogeneic peripheral blood leukocytes expressing HLA alloantigens, said allogeneic peripheral blood leukocytes having been depleted of antigen-presenting cells; and measuring the production of IL-2 by the CD4+ T helper cells of said peripheral blood leukocytes in response to said allogeneic peripheral blood leukocytes;

wherein:

non-responsiveness by the CD4+ T helper cells of said peripheral blood leukocytes being predictive of non-rejection of organ transplant; and responsiveness by the CD4+ T helper cells of said peripheral blood leukocytes being predictive of acute or chronic organ transplant rejection.

* * * * *